(12) United States Patent
Brown et al.

(10) Patent No.: US 7,396,834 B2
(45) Date of Patent: Jul. 8, 2008

(54) 4(PHENYL-PIPERAZINYL-METHYL) BENZAMIDE DERIVATIVES AND THEIR USE FOR THE TREATMENT OF PAIN OR GASTROINTESTINAL DISORDERS

(75) Inventors: William Brown, Blainville (CA); Andrew Griffin, Montreal (CA); Niklas Plobeck, Stockholm (SE); Christopher Walpole, Hudson (CA)

(73) Assignee: AstraZeneca AB, Sodertalje (SE)

( * ) Notice: Subject to any disclaimer, the term of this patent is extended or adjusted under 35 U.S.C. 154(b) by 360 days.

(21) Appl. No.: 10/533,744

(22) PCT Filed: Nov. 5, 2003

(86) PCT No.: PCT/SE03/01703

§ 371 (c)(1),
(2), (4) Date: May 4, 2005

(87) PCT Pub. No.: WO2004/041800

PCT Pub. Date: May 21, 2004

(65) Prior Publication Data

US 2006/0167004 A1    Jul. 27, 2006

(30) Foreign Application Priority Data

Nov. 7, 2002   (SE) ..................... 0203300

(51) Int. Cl.
A61K 31/495    (2006.01)
A61K 31/496    (2006.01)
C07D 295/155   (2006.01)
C07D 307/52    (2006.01)

(52) U.S. Cl. ............... 514/254.1; 514/252.13; 514/253.01; 514/254.02; 514/254.05; 514/255.04; 514/254.01; 544/360; 544/363; 544/369; 544/370; 544/372; 544/379; 544/396

(58) Field of Classification Search .............. None
See application file for complete search history.

(56) References Cited

U.S. PATENT DOCUMENTS

| | | | |
|---|---|---|---|
| 3,940,386 A | 2/1976 | Szabo et al. | |
| 4,778,789 A | 10/1988 | Fex et al. | |
| 5,574,159 A | 11/1996 | Chang et al. | |
| 5,658,908 A | 8/1997 | Chang et al. | |
| 5,681,830 A | 10/1997 | Chang et al. | |
| 5,807,858 A | 9/1998 | Chang et al. | |
| 5,840,896 A | 11/1998 | Van Belle et al. | |
| 5,854,249 A | 12/1998 | Chang et al. | |
| 6,130,222 A | 10/2000 | Roberts et al. | |
| 6,680,318 B2 | 1/2004 | Brown et al. | |
| 6,680,321 B1 | 1/2004 | Roberts et al. | |
| 6,696,447 B2 | 2/2004 | Brown et al. | |
| 6,784,181 B2 | 8/2004 | Brown et al. | |
| 7,030,124 B2 | 4/2006 | Chang et al. | |
| 2006/0030569 A1 | 2/2006 | Brown et al. | |

FOREIGN PATENT DOCUMENTS

| | | |
|---|---|---|
| DE | 2431178 | 1/1975 |
| DE | 2900810 | 7/1980 |
| EP | 0133323 | 2/1985 |
| EP | 0166302 | 1/1986 |
| EP | 0283310 | 9/1988 |
| EP | 0289227 | 11/1988 |
| EP | 0624584 | 8/1998 |
| FR | 2696744 | 4/1994 |
| GB | 2076403 | 12/1981 |
| GB | 2210366 | 6/1989 |
| HU | 215847 | 4/1999 |
| HU | 217619 | 3/2000 |
| JP | 7-138230 | 5/1995 |
| JP | 7138230 | 5/1995 |
| WO | WO 86/04584 | 8/1986 |
| WO | WO 91/07967 | 6/1991 |
| WO | WO 92/04338 | 3/1992 |
| WO | 9206971 | 4/1992 |
| WO | WO 93/15062 | 8/1993 |
| WO | WO 95/04051 | 2/1995 |
| WO | 9626196 | 8/1996 |
| WO | WO 97/23466 | 7/1997 |
| WO | WO 98/28270 | 7/1998 |
| WO | WO 98/28275 | 7/1998 |
| WO | WO 99/33806 | 7/1999 |
| WO | 0146263 | 6/2001 |
| WO | WO 01/45637 | 6/2001 |
| WO | WO 01/46174 | 6/2001 |
| WO | WO 01/74805 | 10/2001 |
| WO | 02094786 | 11/2002 |
| WO | 02094812 | 11/2002 |

(Continued)

OTHER PUBLICATIONS

U.S. Appl. No. 10/714,447, filed Nov. 17, 2003.
U.S. Appl. No. 10/477,642, a PCT national phase filed May 16, 2002.
U.S. Appl. No. 10/533,654, a PCT national phase filed Nov. 5, 2003.
U.S. Appl. No. 10/533,764, a PCT national phase filed Nov. 5, 2003
Bilsky et al., "SNC 80, A Selective, Nonpeptidic and Systemically Active Opioid Delta Agonist," J. Pharmacol. Experi. Ther. 273:359-366 (1995).
Takemori et al., "Selective Natrexone-Drived Opioid Receptor Antagonists," Annu. Rev. Pharmacol. Toxicol. 32:239-269 (1992).
Bilsky et al., "Characterization of Enantiomers of (+) BW373U86 and Related Compounds: Highly Selective Non-Peptidic Delta Opioid Agonists," Reg. Peptides 54:25-26 (1994).
Calderon et al., "Probes for Narcotic Receptor Mediated Phenomena. 19. Synthesis of . . . Opioid Receptor Agonist," J. Med. Chem. 37:2125-2128 (1994).
Calderon et al., "Probes for Narcotic Receptor Mediated Phenomena. 23. Synthesis . . . Opioid Receptor Ligands," J. Med. Chem. 40:695-704 (1997).

(Continued)

*Primary Examiner*—Emily Bernhardt
(74) *Attorney, Agent, or Firm*—Jacqueline M. Cohen

(57) ABSTRACT

Compounds of general formula: wherein $R^1$ and $R^2$ are as defined in the specification, as well as salts, enantiomers thereof and pharmaceutical compositions including the compounds are prepared. They are useful in therapy, in particular in the management of pain.

9 Claims, No Drawings

FOREIGN PATENT DOCUMENTS

| WO | WO 02/094794 | 11/2002 |
|----|--------------|---------|
| WO | WO 03/029215 | 4/2003 |
| WO | 03094853 | 11/2003 |
| WO | 2004041802 | 5/2004 |
| WO | WO 2004/041800 | 5/2004 |
| WO | WO 2004/041801 | 5/2004 |
| WO | 2004062562 | 7/2004 |
| WO | WO 2005/066148 | 7/2005 |
| WO | 2006014133 | 2/2006 |
| WO | 2006091160 | 8/2006 |

OTHER PUBLICATIONS

Chang et al., "A Novel, Potent and Selective Nonpeptidic Delta Opioid Receptor Agonist BW373U86," J. Pharmacol. Exper. Therap. 267:852-857 (1993).

Katrizky et al., "Benzotriazole-Mediated Arylalkylation and Heteroarylalkylation," Chem. Soc. Rev. 23:363-373 (1994).

Kingsbury et al., "Synthesis of Structural Analogs of Leukotriene B and their Receptor Binding Activity," J. Med. Chem. 36:3308-3320 (1993).

Lopez et al., "Exploring the Structure-Activity Relationships . . . Opioid Receptor Nonpeptide Agonist Ligand," J. Med. Chem. 42:5359-5368 (1999).

Plobeck et al., "New Diarylmethylpiperazines as Potent and Selective Nonpeptidic Opioid Receptor Agonists with Increased In Vitro Metabolic Stability," J. Med. Chem. 43:3878-3894 (2000).

Suggs et al., "Facile Synthesis fo 8-Substituted Quinolines," J. Org. Chem., 45:1514-1515 (1980).

Zhang et al., "Probes for Narcotic Receptor Mediated Phenomena. 26. Synthesis . . . Opioid Receptor Ligands," J. Med. Chem. 42:5455-5463 (1999).

English Abstract for FR2696744, (1994).

English Abstract for DE2431178, (1975).

English Abstract for DE2900810, (1980).

English Abstract for JP07138230, (1995).

Burkey et al., "The Efficacy of Delta-Opioid Receptor-Selective Drugs," Medline Abstract for Life Sci. 62:1531-1536 (1998).

Nagase et al., "The Pharmacological Profile of Delta Opioid Receptor Ligands, (+) and (-) TAN-67 on Pain Modulation," Medline Abstract for Life Sci. 68:2227-2231 (2001).

Green, "Protective Groups in Organic Synthesis," pp. 267-268 and 331 (1981).

Abstract for HU 217619, (2000).

Abstract for HU 215847, (1999).

Nortey et al., "Piperazinyl Benzamidines: Synthesis and Affinity for the Delta Opioid Receptor," Bioorganic & Medicinal Chemistry Letters, vol. 11, pp. 1741-1743 (2001).

Snyder et al., "Historical Review: Opioid Receptors," Trends in Pharmacological Sciences, vol. 24, pp. 198-205 (2003).

Adriaensen, H. et al., "Clinical Review of Oral Drug Treatments for Diabetic Neuropathic Pain-Clinical Outcomes Based on Efficacy and Safety Data from Placebo-Controlled and Direct Comparative Studies," Diabetes Metab. Res. Rev., 2005, 21(3), pp. 231-240.

Banker, G. et al., "Modern Pharmaceutics, 3ed.", Marcel Dekker, New York, 1996, pp. 451 and 596.

Davis, MP et al., "Controversies in Pharmacotherapy of Pain Management," Lancet Oncol., 2005, 6(9), pp. 696-704.

Filliol, D. et al., "Mice deficient for delta- and mu-opioid receptors exhibit opposing alternations of emotional responses," Nature Genetics, 2000, vol. 25, pp. 195-200.

Przewlocki, R. et al., "Opioids in Neuropathic Pain," Curr. Pharm. Des. 2005, 11(23), pp. 3013-3025.

Saitoch, A., "Potential anxiolytic and antidepressant-like activities of SNC80, a selective delta-opioid agonist, in behavorial models in rodents," J. Pharmacol. Sci., 2004, vol. 95, pp. 374-380.

Vippagunta, S. et al., "Crystalline Solids," Advanced Drug Delivery Reviews, 2001, vol. 48, pp. 3-26.

West, A., "Solid State Chemistry and its Applications," Wiley, New York, 1988, pp. 358 & 365.

Wolff, M., "Burger's Medicinal Chemistry and Drug Discovery, 5ed, Part 1," John Wiley & Sons, 1995, pp. 975-977.

International Search Report issued for PCT/SE03/01703 on Feb. 24, 2004.

Non-final Office Action issued for U.S. Appl. No. 10/714,447, filed Sep. 10, 2004.

Final Office Action issued for U.S. Appl. No. 10/714,447, filed Mar. 22, 2005.

Advisory Action issued for U.S. Appl. No. 10/714,447, filed Jul. 5, 2005.

Non-final Office Action issued for U.S. Appl. No. 10/714,447, filed Sep. 9, 2005.

Final Office Action issued for U.S. Appl. No. 10/714,447, filed Feb. 16, 2006.

Non-final Office Action issued for U.S. Appl. No. 10/477,642, filed Jan. 13, 2005.

Non-final Office Action issued for U.S. Appl. No. 10/477,642, filed Jun. 15, 2005.

Final Office Action issued for U.S. Appl. No. 10/477,642, filed Nov. 25, 2005.

Non-final Office Action issued for U.S. Appl. No. 10/477,642, filed Apr. 6, 2006.

Non-final Office Action issued for U.S. Appl. No. 10/533,654, filed Apr. 25, 2006.

Non-final Office Action issued for U.S. Appl. No. 10/533,654, filed Dec. 1, 2006.

Non-final Office Action issued for U.S. Appl. No. 10/533,764, filed Apr. 17, 2006.

Final Office Action issued for U.S. Appl. No. 10/533,764, filed Oct. 2, 2006.

Advisory Action issued for U.S. Appl. No. 10/533,764, filed Jan. 10, 2007.

Non-final Office Action issued for U.S. Appl. No. 11/243,623, filed Dec. 7, 2005.

Final Office Action issued for U.S. Appl. No. 11/243,623, filed Jun. 12, 2006.

Non-final Office Action issued for U.S. Appl. No. 11/243,623, filed Aug. 29, 2006.

Final Office Action issued for U.S. Appl. No. 11/243,623, filed May 17, 2007.

Non-final Office Action issued for U.S. Appl. No. 11/243,623, filed Sep. 24, 2007.

Non-final Office Action issued for U.S. Appl. No. 11/743,824, filed Sep. 10, 2007.

Co-pending U.S. Appl. No. 10/596,851, filed May 29, 2007.

Co-pending U.S. Appl. No. 11/572,948, filed Jan. 30, 2007.

Co-pending U.S. Appl. No. 11/743,824, filed May 3, 2007.

Co-pending U.S. Appl. No. 11/774,935, filed Jul. 9, 2007.

Co-pending U.S. Appl. No. 11/816,656, filed Aug. 20, 2007.

4(PHENYL-PIPERAZINYL-METHYL) BENZAMIDE DERIVATIVES AND THEIR USE FOR THE TREATMENT OF PAIN OR GASTROINTESTINAL DISORDERS

CROSS-REFERENCE TO RELATED APPLICATIONS

This application is a U.S. National Stage under 35 U.S.C § 371 of International Application No. PCT/SE2003/001703, filed on 05 Nov. 2003, which claims priority under 35 U.S.C. § 119(a)-(d) to Swedish Application No. 0203300-9 filed on 07 Nov. 2002.

BACKGROUND OF THE INVENTION

1. Field of the Invention

The present invention is directed to novel compounds, to a process for their preparation, their use and pharmaceutical compositions comprising the novel compounds. The novel compounds are useful in therapy, and in particular for the treatment of pain, anxiety and functional gastrointestinal disorders.

2. Discussion of Relevant Art

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors (μ, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. One example of a non-peptidic δ-agonist is SNC80 (Bilsky E. J. et al., Journal of Pharmacology and Experimental Therapeutics, 273(1), pp. 359-366 (1995)).

Many δ agonist compounds that have been identified in the prior art have many disadvantages in that they suffer from poor pharmacokinetics and are not analgesic when administered by systemic routes. Also, it has been documented that many of these δ agonist compounds show significant convulsive effects when administered systemically.

U.S. Pat. No. 6,130,222 to Roberts et al. describes some δ-agonists.

However, there is still a need for improved δ-agonists.

DETAILED DESCRIPTION OF THE INVENTION

Definitions

Unless specified otherwise within this specification, the nomenclature used in this specification generally follows the examples and rules stated in *Nomenclature of Organic Chemistry, Sections A, B, C, D, E, F, and H*, Pergamon Press, Oxford, 1979, which is incorporated by references herein for its exemplary chemical structure names and rules on naming chemical structures.

The term "$C_{m-n}$" or "$C_{m-n}$ group" used alone or as a prefix, refers to any group having m to n carbon atoms.

The term "hydrocarbon" used alone or as a suffix or prefix, refers to any structure comprising only carbon and hydrogen atoms up to 14 carbon atoms.

The term "hydrocarbon radical" or "hydrocarbyl" used alone or as a suffix or prefix, refers to any structure as a result of removing one or more hydrogens from a hydrocarbon.

The term "alkyl" used alone or as a suffix or prefix, refers to monovalent straight or branched chain hydrocarbon radicals comprising 1 to about 12 carbon atoms. An "alkyl" may optionally contain one or more unsaturated carbon-carbon bonds.

The term "alkylene" used alone or as suffix or prefix, refers to divalent straight or branched chain hydrocarbon radicals comprising 1 to about 12 carbon atoms, which serves to links two structures together.

The term "alkenyl" used alone or as suffix or prefix, refers to a monovalent straight or branched chain hydrocarbon radical having at least one carbon-carbon double bond and comprising at least 2 up to about 12 carbon atoms.

The term "alkynyl" used alone or as suffix or prefix, refers to a monovalent straight or branched chain hydrocarbon radical having at least one carbon-carbon triple bond and comprising at least 2 up to about 12 carbon atoms.

The term "cycloalkyl," used alone or as suffix or prefix, refers to a monovalent ring-containing hydrocarbon radical comprising at least 3 up to about 12 carbon atoms.

The term "cycloalkenyl" used alone or as suffix or prefix, refers to a monovalent ring-containing hydrocarbon radical having at least one carbon-carbon double bond and comprising at least 3 up to about 12 carbon atoms.

The term "cycloalkynyl" used alone or as suffix or prefix, refers to a monovalent ring-containing hydrocarbon radical having at least one carbon-carbon triple bond and comprising about 7 up to about 12 carbon atoms.

The term "aryl" used alone or as suffix or prefix, refers to a monovalent hydrocarbon radical having one or more polyunsaturated carbon rings having aromatic character, (e.g., 4n+2 delocalized electrons) and comprising 5 up to about 14 carbon atoms.

The term "arylene" used alone or as suffix or prefix, refers to a divalent hydrocarbon radical having one or more polyunsaturated carbon rings having aromatic character, (e.g., 4n+2 delocalized electrons) and comprising 5 up to about 14 carbon atoms, which serves to link two structures together.

The term "heterocycle" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heteroaromatic" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s), wherein the ring-containing structure or molecule has an aromatic character (e.g., 4n+2 delocalized electrons).

The term "heterocyclic group," "heterocyclic moiety," "heterocyclic," or "heterocyclo" used alone or as a suffix or prefix, refers to a radical derived from a heterocycle by removing one or more hydrogens therefrom.

The term "heterocyclyl" used alone or as a suffix or prefix, refers a monovalent radical derived from a heterocycle by removing one hydrogen therefrom.

The term "heterocyclylene" used alone or as a suffix or prefix, refers to a divalent radical derived from a heterocycle by removing two hydrogens therefrom, which serves to links two structures together.

The term "heteroaryl" used alone or as a suffix or prefix, refers to a heterocyclyl having aromatic character.

The term "heterocylcoalkyl" used alone or as a suffix or prefix, refers to a heterocyclyl that does not have aromatic character.

The term "heteroarylene" used alone or as a suffix or prefix, refers to a heterocyclylene having aromatic character.

The term "heterocycloalkylene" used alone or as a suffix or prefix, refers to a heterocyclylene that does not have aromatic character.

The term "six-membered" used as prefix refers to a group having a ring that contains six ring atoms.

The term "five-membered" used as prefix refers to a group having a ring that contains five ring atoms.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

The term "substituted" used as a prefix refers to a structure, molecule or group, wherein one or more hydrogens are replaced with one or more $C_{1-6}$hydrocarbon groups, or one or more chemical groups containing one or more heteroatoms selected from N, O, S, F, Cl, Br, I, and P. Exemplary chemical groups containing one or more heteroatoms include —$NO_2$, —OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, —C(=O)$NR_2$, —NRC(=O)R, oxo (=O), imino (=NR), thio (=S), and oximino (=N—OR), wherein each "R" is a $C_{1-6}$hydrocarbyl. For example, substituted phenyl may refer to nitrophenyl, methoxyphenyl, chlorophenyl, aminophenyl, etc., wherein the nitro, methoxy, chloro, and amino groups may replace any suitable hydrogen on the phenyl ring.

The term "substituted" used as a suffix of a first structure, molecule or group, followed by one or more names of chemical groups refers to a second structure, molecule or group, which is a result of replacing one or more hydrogens of the first structure, molecule or group with the one or more named chemical groups. For example, a "phenyl substituted by nitro" refers to nitrophenyl.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles, for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pynmidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl; 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "alkoxy" used alone or as a suffix or prefix, refers to radicals of the general formula —O—R, wherein R is selected from a hydrocarbon radical. Exemplary alkoxy includes methoxy, ethoxy, propoxy, isopropoxy, butoxy, t-butoxy, isobutoxy, cyclopropylmethoxy, allyloxy, and propargyloxy.

The term "amine" or "amino" used alone or as a suffix or prefix, refers to radicals of the general formula —NRR', wherein R and R' are independently selected from hydrogen or a hydrocarbon radical.

Halogen includes fluorine, chlorine, bromine and iodine.

"Halogenated," used as a prefix of a group, means one or more hydrogens on the group is replaced with one or more halogens.

"RT" or "rt" means room temperature.

In one aspect, the invention provides a compound of formula I, enantiomers thereof, diastereomers thereof and pharmaceutically acceptable salts thereof:

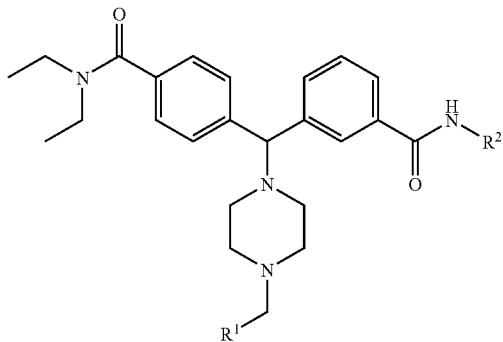

I wherein
R$^1$ is an aryl, heteroaryl, substituted aryl or substituted heteroaryl; and
R$^2$ is hydrogen, optionally substituted C$_{1-12}$alkyl, optionally substituted C$_{6-12}$aryl, or optionally substituted C$_{2-12}$heterocyclyl.

In one embodiment, the present invention provides a compound of formula I,
wherein R$^1$ is selected from phenyl; pyridyl; thienyl; furyl; imidazolyl; triazolyl; pyrrolyl; thiazolyl; and N-oxido-pyridyl, optionally substituted with one or more groups selected from C$_{1-6}$alkyl, halogenated C$_{1-6}$alkyl, —NO$_2$, —CF$_3$, C$_{1-6}$ alkoxy, chloro, fluoro, bromo, and iodo; and
R$^2$ is hydrogen or methyl.

In another embodiment, the present invention provides a compound of formula I,
wherein R$^1$ is selected from phenyl; pyridyl; thienyl; furyl; imidazolyl; pyrrolyl; and thiazolyl, optionally substituted with one or more groups selected from C$_{1-6}$alkyl, halogenated C$_{1-6}$alkyl, —NO$_2$, —CF$_3$, C$_{1-6}$ alkoxy, chloro, fluoro, bromo, and iodo; and
R$^2$ is hydrogen or methyl.

In a further embodiment, the present invention provides a compound of formula I,
wherein R$^1$ is selected from phenyl; pyridyl; thienyl; furyl; imidazolyl; pyrrolyl; and thiazolyl; and
R$^2$ is hydrogen or methyl.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be appreciated that certain compounds of the present invention may exist as geometrical isomers, for example E and Z isomers of alkenes. The present invention includes any geometrical isomer of a compound of Formula I. It will further be understood that the present invention encompasses tautomers of the compounds of the formula I.

It will also be understood that certain compounds of the present invention may exist in solvated, for example hydrated, as well as unsolvated forms. It will further be understood that the present invention encompasses all such solvated forms of the compounds of the formula I.

Within the scope of the invention are also salts of the compounds of the formula I. Generally, pharmaceutically acceptable salts of compounds of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of formula I above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

The novel compounds of the present invention are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (ET).

Compounds of the invention are useful for the treatment of diarrhoea, depression, anxiety and stress-related disorders such as post-traumatic stress disorders, panic disorder, generalized anxiety disorder, social phobia, and obsessive compulsive disorder, urinary incontinence, premature ejaculation, various mental illnesses, cough, lung oedema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following miocardial infarction, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment.

Thus, the invention provides a compound of formula I, or pharmaceutically acceptable salt or solvate thereof, as hereinbefore defined for use in therapy.

In a further aspect, the present invention provides the use of a compound of formula I, or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The term "therapeutic" and "therapeutically" should be contrued accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

The compounds of the present invention are useful in therapy, especially for the therapy of various pain conditions including, but not limited to: chronic pain, neuropathic pain, acute pain, back pain, cancer pain, and visceral pain.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the invention, the route of administration may be orally, intravenously or intramuscularly.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid and liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (percent by weight), more preferably from 0.10 to 50% w, of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

Within the scope of the invention is the use of any compound of formula I as defined above for the manufacture of a medicament.

Also within the scope of the invention is the use of any compound of formula I for the manufacture of a medicament for the therapy of pain.

Additionally provided is the use of any compound according to Formula I for the manufacture of a medicament for the therapy of various pain conditions including, but not limited to: chronic pain, neuropathic pain, acute pain, back pain, cancer pain, and visceral pain.

A further aspect of the invention is a method for therapy of a subject suffering from any of the conditions discussed above, whereby an effective amount of a compound according to the formula I above, is administered to a patient in need of such therapy.

Additionally, there is provided a pharmaceutical composition comprising a compound of Formula I, or a pharmaceutically acceptable salt thereof, in association with a pharmaceutically acceptable carrier.

Particularly, there is provided a pharmaceutical composition comprising a compound of Formula I, or a pharmaceutically acceptable salt thereof, in association with a pharmaceutically acceptable carrier for therapy, more particularly for therapy of pain.

Further, there is provided a pharmaceutical composition comprising a compound of Formula I, or a pharmaceutically acceptable salt thereof, in association with a pharmaceutically acceptable carrier use in any of the conditions discussed above.

In a further aspect, the present invention provides a method of preparing a compound of formula I.

In one embodiment, the invention provides a process for preparing a compound of formula II,

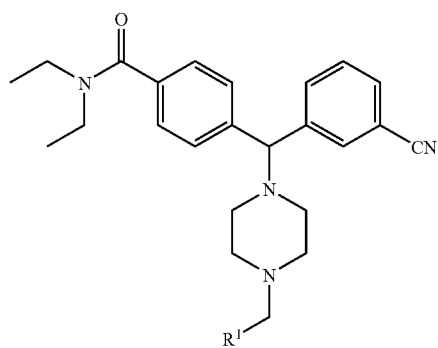

II comprising of the step of reacting a compound of formula III:

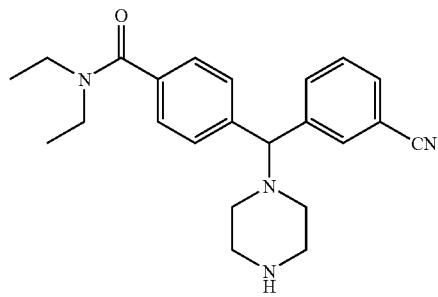

III with R¹—CHO to form the compound of formula II wherein

R¹ is an aryl, heteroaryl, substituted aryl or substituted heteroaryl.

In another embodiment, the invention provides a process for preparing a compound of formula IV,

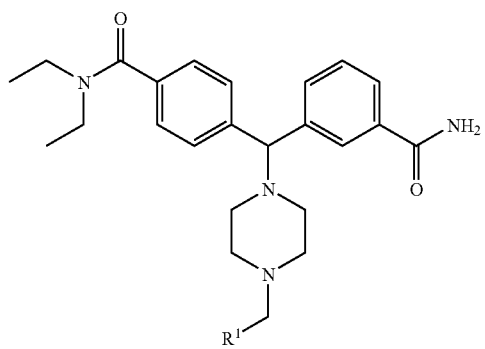

IV comprising: reacting a compound of formula II,

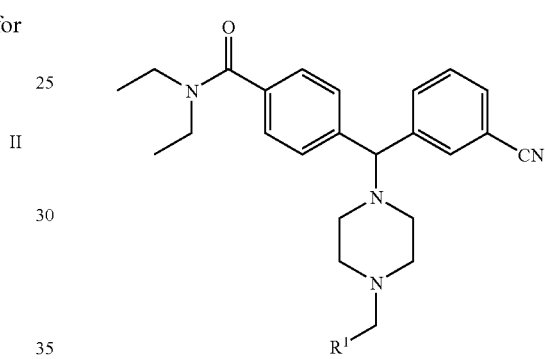

II with an alkali metal hydroxide in non-aqueous solvent to form the compound of formula IV:

wherein

R¹ is an aryl, heteroaryl, substituted aryl or substituted heteroaryl.

Particularly, the compounds of the present invention can be prepared according to the synthetic routes as exemplified in Schemes 1 and 2.

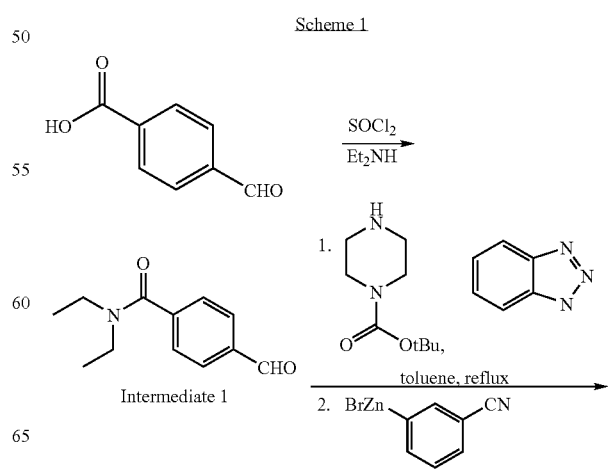

Scheme 1

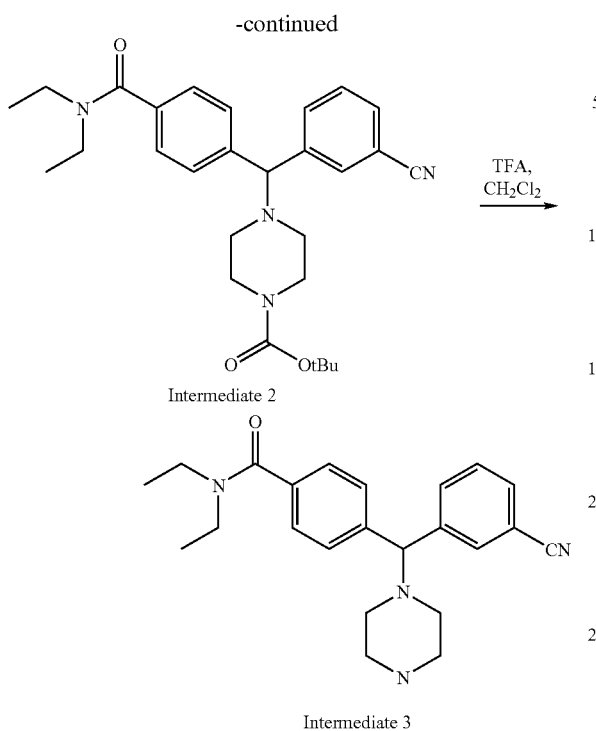
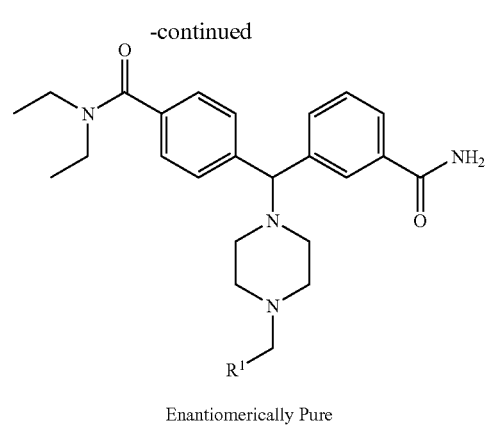
Compound 1a: $R^1$ = phenyl; (−) isomer;
Compound 1b: $R^1$ = phenyl; (+) isomer;
Compound 2a: $R^1$ = 2-furyl; (−) isomer;
Compound 2b: $R^1$ = 2-furyl; (+) isomer.
In another embodiment, the compounds of the present invention can be prepared according to the synthetic routes as exemplified in Schemes 3 and 4.
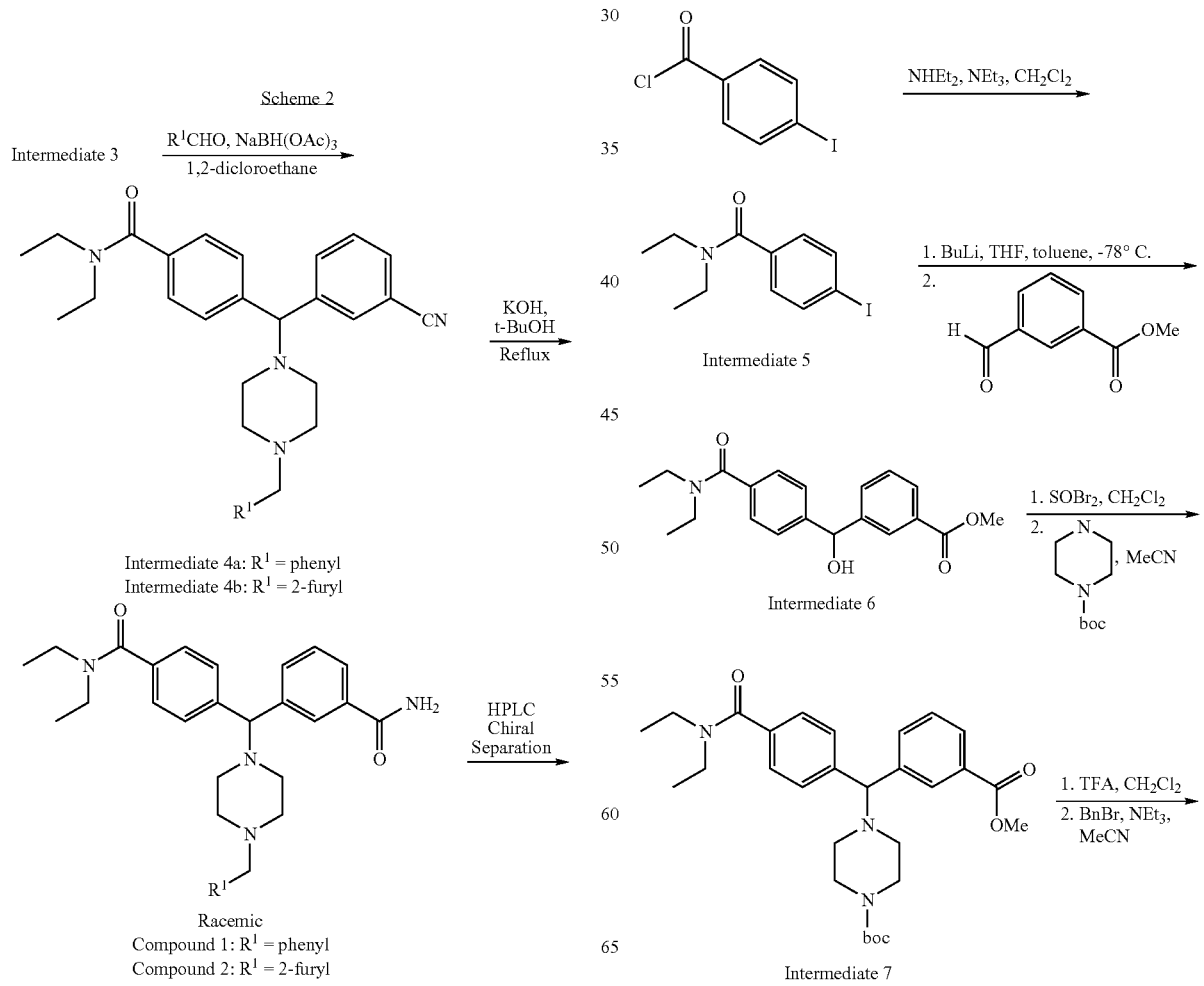

-continued

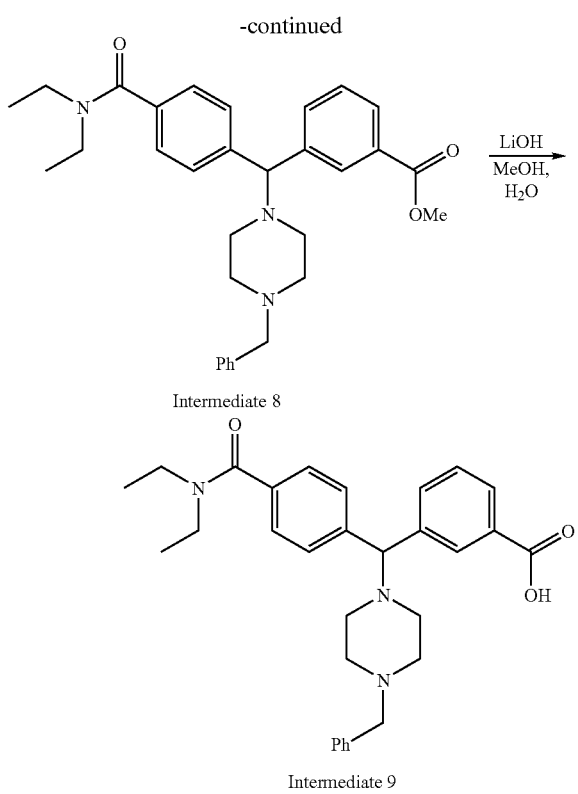

Scheme 4

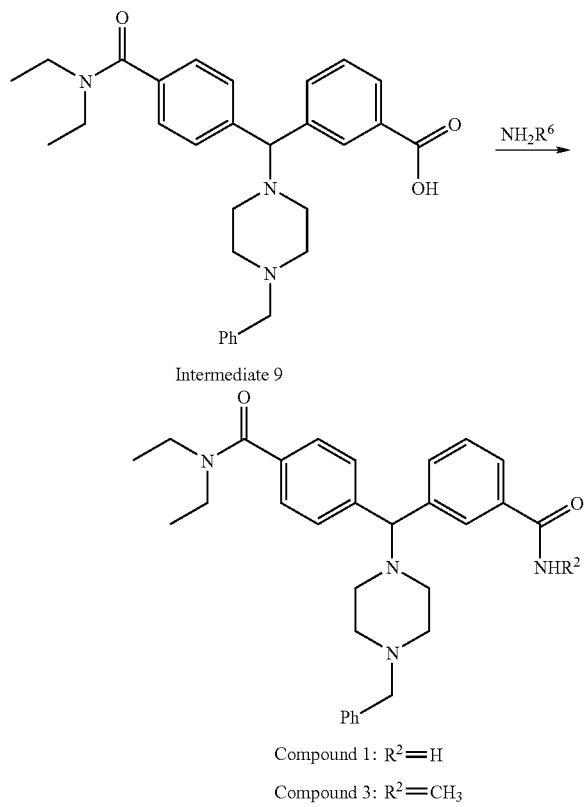

Compound 1: $R^2$=H

Compound 3: $R^2$=CH$_3$

Biological Evaluation

The compounds of the invention are found to be active towards δ receptors in warm-blooded animal, e.g., human. Particularly the compounds of the invention are found to be effective δ receptor ligands. In vitro assays, infra, demonstrate these surprising activities, especially with regard to agonists potency and efficacy as demonstrated in the rat brain functional assay and/or the human δ receptor functional assay (low). This feature may be related to in vivo activity and may not be linearly correlated with binding affinity. In these in vitro assays, a compound is tested for their activity toward δ receptors and IC$_{50}$ is obtained to determine the selective activity for a particular compound towards δ receptors. In the current context, IC$_{50}$ generally refers to the concentration of the compound at which 50% displacement of a standard radioactive δ receptor ligand has been observed.

The activities of the compound towards κ and μ receptors are also measured in a similar assay.

In vitro Model

Cell Culture

Human 293S cells expressing cloned human κ, δ and μ receptors and neomycin resistance are grown in suspension at 37° C. and 5% CO$_2$ in shaker flasks containing calcium-free DMEM10% FBS, 5% BCS, 0.1% Pluronic F-68, and 600 μg/ml geneticin.

Rat brains are weighed and rinsed in ice-cold PBS (containing 2.5 mM EDTA, pH 7.4). The brains are homogenized with a polytron for 30 sec (rat) in ice-cold lysis buffer (50 mM Tris, pH 7.0, 2.5mM EDTA, with phenylmethylsulfonyl fluoride added just prior use to 0.5 MmM from a 0.5M stock in DMSO:ethanol).

Membrane Preparation

Cells are pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension is spun at 1000 g (max) for 10 min at 4° C. The supernatant is saved on ice and the pellets resuspended and spun as before. The supernatants from both spins are combined and spun at 46,000 g(max) for 30 min. The pellets are resuspended in cold Tris buffer (50 mM Tris/Cl, pH 7.0) and spun again. The final pellets are resuspended in membrane buffer (50 mM Tris, 0.32 M sucrose, pH 7.0). Aliquots (1 ml) in polypropylene tubes are frozen in dry ice/ethanol and stored at −70° C. until use. The protein concentrations are determined by a modified Lowry assay with sodium dodecyl sulfate.

Binding Assays

Membranes are thawed at 37° C., cooled on ice, passed 3 times through a 25-gauge needle, and diluted into binding buffer (50 mM Tris, 3 mM MgCl$_2$, 1 mg/ml BSA (Sigma A-7888), pH 7.4, which is stored at 4° C. after filtration through a 0.22 m filter, and to which has been freshly added 5 μg/ml aprotinin, 10 μM bestatin, 10 μM diprotin A, no DTT). Aliquots of 100 μl are added to iced 12×75 mm polypropylene tubes containing 100 μl of the appropriate radioligand and 100 μl of test compound at various concentrations. Total (TB) and nonspecific (NS) binding are determined in the absence and presence of 10 μM naloxone respectively. The tubes are vortexed and incubated at 25° C. for 60-75 min, after which time the contents are rapidly vacuum-filtered and washed with about 12 ml/tube iced wash buffer (50 mM Tris, pH 7.0, 3 mM MgCl$_2$) through GF/B filters (Whatman) presoaked for at least 2 h in 0.1% polyethyleneimine. The radioactivity (dpm) retained on the filters is measured with a beta counter after soaking the filters for at least 12 h in minivials containing 6-7 ml scintillation fluid. If the assay is set up in 96-place deep well plates, the filtration is over 96-place PEI-soaked unifilters, which are washed with 3×1 ml wash buffer, and dried in an oven at 55° C. for 2 h. The filter plates are counted in a TopCount (Packard) after adding 50 μl MS-20 scintillation fluid/well.

Functional Assays

The agonist activity of the compounds is measured by determining the degree to which the compounds receptor complex activates the binding of GTP to G-proteins to which the receptors are coupled. In the GTP binding assay, GTP[γ]$^{35}$S is combined with test compounds and membranes from HEK-293S cells expressing the cloned human opioid receptors or from homogenised rat and mouse brain. Agonists stimulate GTP[γ]$^{35}$S binding in these membranes. The $EC_{50}$ and $E_{max}$ values of compounds are determined from dose-response curves. Right shifts of the dose response curve by the delta antagonist naltrindole are performed to verify that agonist activity is mediated through delta receptors. For human δ receptor functional assays, $EC_{50}$ (low) is measured when the human δ receptors used in the assay were expressed at lower levels in comparison with those used in determining $EC_{50}$ (high). The $E_{max}$ values were determined in relation to the standard δ agonist SNC80, i.e., higher than 100% is a compound that have better efficacy than SNC80.

Procedure for Rat Brain GTP

Rat brain membranes are thawed at 37° C., passed 3 times through a 25-gauge blunt-end needle and diluted in the GTPYS binding (50 mM Hepes, 20 mM NaOH, 100 mM NaCl, 1 mM EDTA, 5 mM MgCl$_2$, pH 7.4, Add fresh: 1 mM DTT, 0.1% BSA). 120 μM GDP final is added membranes dilutions. The $EC_{50}$ and $E_{max}$ of compounds are evaluated from 10-point dose-response curves done in 300 μl with the appropriate amount of membrane protein (20 μg/well) and 100000-130000 dpm of GTPγ$^{35}$S per well (0.11-0.14 nM). The basal and maximal stimulated binding are determined in absence and presence of 3 μM SNC-80.

Data Analysis

The specific binding (SB) was calculated as TB-NS, and the SB in the presence of various test compounds was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean±S.E.M. values of $IC_{50}$, $K_i$ and $n_H$ were reported for ligands tested in at least three displacement curves. Biological activity of the compounds of the present invention is indicated in Tables 1 and 2.

TABLE 1

| Ex. # | Human δ (nM) | | | Human κ $IC_{50}$ | Human μ $IC_{50}$ | RAT BRAIN (nM) | |
|---|---|---|---|---|---|---|---|
| | $IC_{50}$ | $EC_{50}$ (high) | % EMax (high) | | | $EC_{50}$ | % EMax |
| 1a | 0.26 | 0.29 | 101 | 112 | 7.7 | 0.2 | 170 |

TABLE 2

| Ex. # | Human δ (nM) | | | Human κ $IC_{50}$ | Human μ $IC_{50}$ |
|---|---|---|---|---|---|
| | $IC_{50}$ | $EC_{50}$ (low) | % EMax (low) | | |
| 1b, 2a 2b, 3a and 3b | 0.14-3.73 | 0.5-83 | 91-104 | 396 → 10000 | 45-1718 |

Receptor Saturation Experiments

Radioligand Kδ values are determined by performing the binding assays on cell membranes with the appropriate radioligands at concentrations ranging from 0.2 to 5 times the estimated Kδ (up to 10 times if amounts of radioligand required are feasible). The specific radioligand binding is expressed as pmole/mg membrane protein. Values of Kδ and $B_{max}$ from individual experiments are obtained from nonlinear fits of specifically bound (B) vs. nM free (F) radioligand from individual according to a one-site-model.

Determination of Mechano-Allodynia Using Von Frey Testing

Testing is performed between 08:00 and 16:00 h using the method described by Chaplan et al. (1994). Rats are placed in Plexiglas cages on top of a wire mesh bottom which allows access to the paw, and are left to habituate for 10-15 min. The area tested is the mid-plantar left hind paw, avoiding the less sensitive foot pads. The paw is touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair is applied from underneath the mesh floor perpendicular to the plantar surface with sufficient force to cause a slight buckling against the paw, and held for approximately 6-8 seconds. A positive response is noted if the paw is sharply withdrawn. Flinching immediately upon removal of the hair is also considered a positive response. Ambulation is considered an ambiguous response, and in such cases the stimulus is repeated.

Testing Protocol

The animals are tested on postoperative day 1 for the FCA-treated group. The 50% withdrawal threshold is determined using the up-down method of Dixon (1980). Testing is started with the 2.04 g hair, in the middle of the series. Stimuli are always presented in a consecutive way, whether ascending or descending. In the absence of a paw withdrawal response to the initially selected hair, a stronger stimulus is presented; in the event of paw withdrawal, the next weaker stimulus is chosen. Optimal threshold calculation by this method requires 6 responses in the immediate vicinity of the 50% threshold, and counting of these 6 responses begins when the first change in response occurs, e.g. the threshold is first crossed. In cases where thresholds fall outside the range of stimuli, values of 15.14 (normal sensitivity) or 0.41 (maximally allodynic) are respectively assigned. The resulting pattern of positive and negative responses is tabulated using the convention, X=no withdrawal; O=withdrawal, and the 50% withdrawal threshold is interpolated using the formula:

$$50\% \text{ g threshold} = 10^{(Xf+k\delta)}/10,000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds are converted to percent of maximum possible effect (% MPE), according to Chaplan et al. 1994. The following equation is used to compute % MPE:

$$\% \ MPE = \frac{\text{Drug treated threshold }(g) - \text{allodynia threshold }(g)}{\text{Control threshold }(g) - \text{allodynia threshold }(g)} \times 100$$

Administration of Test Substance

Rats are injected (subcutaneously, intraperitoneally, intravenously or orally) with a test substance prior to von Frey testing, the time between administration of test compound and the von Frey test varies depending upon the nature of the test compound.

Writhing Test

Acetic acid will bring abdominal contractions when administered intraperitoneally in mice. These will then extend their body in a typical pattern. When analgesic drugs are administered, this described movement is less frequently observed and the drug selected as a potential good candidate.

A complete and typical Writhing reflex is considered only when the following elements are present: the animal is not in movement; the lower back is slightly depressed; the plantar aspect of both paws is observable. In this assay, compounds of the present invention demonstrate significant inhibition of writhing responses after oral dosing of 1-100 µmol/kg.

(i) Solutions Preparation

Acetic acid (AcOH): 120 µL of Acetic Acid is added to 19.88 ml of distilled water in order to obtain a final volume of 20 ml with a final concentration of 0.6% AcOH. The solution is then mixed (vortex) and ready for injection.

Compound (drug): Each compound is prepared and dissolved in the most suitable vehicle according to standard procedures.

(ii) Solutions Administration

The compound (drug) is administered orally, intraperitoneally (i.p.), subcutaneously (s.c.) or intravenously (i.v.)) at 10 ml/kg (considering the average mice body weight) 20, 30 or 40 minutes (according to the class of compound and its characteristics) prior to testing. When the compound is delivered centrally: Intraventricularly (i.c.v.) or intrathecally (i.t.) a volume of 5 µL is administered.

The AcOH is administered intraperitoneally (i.p.) in two sites at 10 ml/kg (considering the average mice body weight) immediately prior to testing.

(iii) Testing

The animal (mouse) is observed for a period of 20 minutes and the number of occasions (Writhing reflex) noted and compiled at the end of the experiment. Mice are kept in individual "shoe box" cages with contact bedding. A total of 4 mice are usually observed at the same time: one control and three doses of drug.

For the anxiety and anxiety-like indications, efficacy has been established in the geller-seifter conflict test in the rat.

For the functional gastrointestina disorder indication, efficacy can be established in the assay described by Coutinho S V et al, in American Journal of Physiology—Gastrointestinal & Liver Physiology. 282(2):G307-16, February 2002, in the rat.

Additional in vivo Testing Protocols

Subjects and Housing

Naïve male Sprague Dawley rats (175-200 g) are housed in groups of 5 in a temperature controlled room (22° C., 40-70% humidity, 12-h light/dark). Experiments are performed during the light phase of the cycle. Animals have food and water ad libitum and are sacrificed immediately after data acquisition.

Sample

Compound (Drug) testing includes groups of rats that do not receive any treatment and others that are treated with *E. coli* lipopolysaccharide(LPS). For the LPS-treated experiment, four groups are injected with LPS, one of the four groups is then vehicle-treated whilst the other three groups are injected with the drug and its vehicle. A second set of experiments are conducted involving five groups of rats; all of which receive no LPS treatment. The naive group receives no compound (drug) or vehicle; the other four groups are treated with vehicle with or without drug. These are performed to determine anxiolytic or sedative effects of drugs which can contribute to a reduction in USV.

Administration of LPS

Rats are allowed to habituate in the experimental laboratory for 15-20 min prior to treatment. Inflammation is induced by administration of LPS (endotoxin of gram-negative *E. coli* bacteria serotype 0111: B4, Sigma). LPS (2.4 µg) is injected intracerebro-ventricularly (i.c.v.), in a volume of 10 µl, using standard stereotaxic surgical techniques under isoflurane anaesthesia. The skin between the ears is pushed rostrally and a longitudinal incision of about 1 cm is made to expose the skull surface. The puncture site is determined by the coordinates: 0.8 mm posterior to the bregma, 1.5 mm lateral (left) to the lambda (sagittal suture), and 5 mm below the surface of the skull (vertical) in the lateral ventricle. LPS is injected via a sterile stainless steel needle (26-G 3/8) of 5 mm long attached to a 100 µl Hamilton syringe by polyethylene tubing (PE20; 10-15 cm). A 4 mm stopper made from a cut needle (20-G) is placed over and secured to the 26-G needle by silicone glue to create the desired 5 mm depth.

Following the injection of LPS, the needle remains in place for an additional 10 s to allow diffusion of the compound, then is removed. The incision is closed, and the rat is returned to its original cage and allowed to rest for a minimum of 3.5 h-prior to testing.

Experimental Setup for Air-Puff Stimulation

The rats remains in the experimental laboratory following LPS injection and compound (drug) administration. At the time of testing all rats are removed and placed outside the laboratory. One rat at a time is brought into the testing laboratory and placed in a clear box (9×9×18 cm) which is then placed in a sound-attenuating ventilated cubicle measuring 62(w)×35(d)×46(h) cm (BRS/LVE, Div. Tech-Serv Inc). The delivery of air-puffs, through an air output nozzle of 0.32 cm, is controlled by a system (AirStim, San Diego Intruments) capable of delivering puffs of air of fixed duration (0.2 s) and fixed intensity with a frequency of 1 puff per 10 s. A maximun of 10 puffs are administered, or until vocalisation starts, which ever comes first. The first air puff marks the start of recording.

Experimental Setup for and Ultrasound Recording

The vocalisations are recorded for 10 minutes using microphones (G.R.A.S. sound and vibrations, Vedbaek, Denmark) placed inside each cubicle and controlled by LMS (LMS CADA-X 3.5B, Data Acquisition Monitor, Troy, Mich.) software. The frequencies between 0 and 32000 Hz are recorded, saved and analysed by the same software (LMS CADA-X 3.5B, Time Data Processing Monitor and UPA (User Programming and Analysis)).

Compounds (Drugs)

All compounds (drugs) are pH-adjusted between 6.5 and 7.5 and administered at a volume of 4 ml/kg. Following compound (drug) administration, animals are returned to their original cages until time of testing.

Analysis

The recording is run through a series of statistical and Fourier analyses to filter (between 20-24 kHz) and to calculate the parameters of interest. The data are expressed as the mean ±SEM. Statistical significance is assessed using T-test for comparison between naive and LPS-treated rats, and one way ANOVA followed by Dunnett's multiple comparison test (post-hoc) for drug effectiveness. A difference between groups is considered significant with a minimum p value of ≦0.05. Experiments are repeated a minimum of two times.

EXAMPLES

The invention will further be described in more detail by the following Examples which describe methods whereby compounds of the present invention may be prepared, purified, analyzed and biologically tested, and which are not to be construed as limiting the invention.

INTERMEDIATE 1:
N,N-Diethyl-4-formylbenzamide

To a suspension of 4-carboxybenzaldehyde (30 g, 0.2 mole) in 100 ml of toluene was added $SOCl_2$ (97 ml, 1.3 moles) at 60° C. The reaction was heated until gas evolution ceased followed by evaporation to dryness with toluene (3×50 mL) This yielded a residue, which was dissolved in $CH_2Cl_2$ (200 mL). To this solution, cooled in an ice bath while stirring, was added diethylamine (50 mL). Stirring was continued for one hour and then the mixture heated at reflux for a further hour. After cooling, the mixture was washed successively with $H_2O$, 2 N HCl, $H_2O$ then 2 N NaOH and finally with $H_2O$. The solution was dried over $MgSO_4$, filtered and concentrated to dryness yielding 41 g of oil. Distillation at 140-150° C./1.5 torr gave 36.9 g, 90% of INTERMEDIATE 1.

INTERMEDIATE 2: 1-piperazinecarboxylic acid, 4-[(3-cyanophenyl)[4-[(diethylamino)carbonyl]phenyl]methyl]-,1,1-dimethylethyl ester To a dry flask containing N,N-diethyl-4-formyl-benzamide (INTERMEDIATE 1) (1.60 g, 1 eq), benzotriazole (929 mg, 1 eq) and 1-piperazinecarboxylic acid, 1,1-dimethylethyl ester (1.45 g, 1 eq) was added dry toluene (50 mL) and the reaction was heated to reflux with water removal. After 3.5 hours the reaction was cooled and concentrated to approximately 5 mL. The solution was diluted with tetrahydrofuran (5 mL) and added slowly to a flask containing 3-cyanophenylzinc iodide (0.37 M solution in tetrahydrofuran, 42 mL, 2 eq). The reaction was heated to 50° C. for 20 hours then was cooled and quenched with saturated aqueous ammonium chloride (50 mL). After 10 minutes the mixture was extracted with dichloromethane (2×100 mL) and the combined organic extracts were then dried ($MgSO_4$), filtered and concentrated. The residue was purified by flash chromatography, eluting 3% methanol in dichloromethane to yield INTERMEDIATE 2 as a yellow oil (2.120 g).

INTERMEDIATE 3: 4-[(3-cyanophenyl)-1-piperazinylmethyl]-N,N-diethyl-benzamide

To a solution of INTERMEDIATE 2 (2.120 g) in dichloromethane (40 mL) was added trifluoroacetic acid (6.5 mL, 15 eq). After three hours at room temperature the reaction was quenched with aqueous sodium hydroxide solution (1 N, 40 mL) and the organic layer was separated. The aqueous layer was washed with dichloromethane (2×50 mL) and the combined organic extracts were dried ($MgSO_4$), filtered and concentrated. The residue was purified by flash chromatography, eluting 10% to 20% methanol in dichloromethane to yield INTERMEDIATE 3 as a colorless foam (1.113 g, 39% over 3 steps).

INTERMEDIATE 4a: 3-[(4-[(diethylamino)carbonyl]phenyl)(4-benzyl-piperazin-1-yl)methyl]benzonitrile

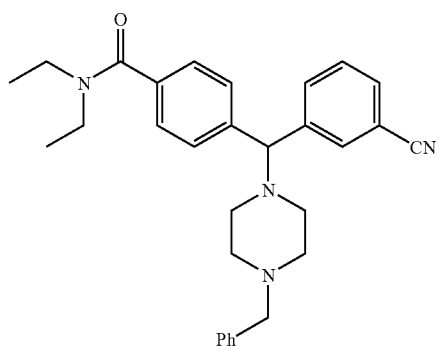

To a solution of INTERMEDIATE 3 (606 mg) in 1,2-dichloroethane (15 mL) was added benzaldehyde (220 μL, 1.3 eq) and sodium triacetoxyborohydride (480 mg, 1.4 eq). After 3 days the reaction was diluted with dichloromethane (50 mL) and washed with saturated aqueous sodium bicarbonate. The aqueous layer was washed with dichloromethane (2×25 mL) and the combined organic extracts were dried ($MgSO_4$), filtered and concentrated. The residue was purified by flash chromatography, eluting 5% methanol in dichloromethane to yield INTERMEDIATE 4a as a colorless foam (428mg, 57%).

INTERMEDIATE 4b: 3-{(4-[(diethylamino)carbonyl]phenyl)[4-(2-furylmethyl)-piperazin-1-yl]methyl}benzonitrile

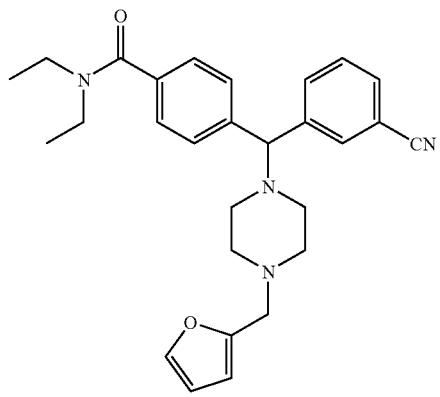

To a solution of INTERMEDIATE 3 (567 mg) in 1,2-dichloroethane (15 mL) was added 2-furaldehyde (160 μL, 1.3 eq) and sodium triacetoxyborohydride (450 mg, 1.4 eq). After 3 days the reaction was diluted with dichloromethane (50 mL) and washed with saturated aqueous sodium bicarbonate. The aqueous layer was washed with dichloromethane (2×25 mL) and the combined organic extracts were dried ($NgSO_4$), filtered and concentrated. The residue was purified by flash chromatography, eluting 5% methanol in dichloromethane to yield INTERMEDIATE 4b as a colorless foam (367 mg, 53%).

INTERMEDIATE 5: 4-Iodo-N,N-diethylbenzamide

To a mixture of 4-iodo-benzoyl chloride (75 g) in 500 mL $CH_2Cl_2$ was added a mixture of $Et_3N$ (50 mL) and $Et_2NH$ (100 mL) at 0° C. After the addition, the resulting reaction mixture was warmed up to room temperature in 1 hr and was then washed with saturated ammonium chloride. The organic extract was dried ($Na_2SO_4$), filtered and concentrated. Residue was recrystallized from hot hexanes to give 80 g of INTERMEDIATE 5.

INTERMEDIATE 6: 3-[[4-[(diethylamino)carbonyl]phenyl]hydroxymethyl]-benzoic acid, methyl ester INTERMEDIATE 5 (2.8 g, 9.0 mmol) was dissolved in TBF (100 mL) and cooled to −78° C. under nitrogen atmosphere. Then n-BuLi (8.4 mL, 1.07 M solution in hexane, 9.0 mmol) was added dropwise during 10 min at −65 to −78° C. The solution was canulated into 3-carbomethoxybenzaldehyde (1.49 g, 9.1 mmol) in toluene/THF (approx. 1:1, 50 mL) at −78° C. $NH_4Cl$ (aq.) was added after 30 min. After concentration in vacuo, extraction with EtOAc/water, drying ($MgSO_4$) and evaporation of the organic phase, the residue was purified by chromatography on silica (0-75% EtOAc/heptane) to give INTERMEDIATE 6 (1.5 g, 49%).

INTERMEDIATE 7: 1-piperazinecarboxylic acid, 4-[[4-[(diethylamino)carbonyl]phenyl][3-(methoxycarbonyl)phenyl]methyl]-,1,1-dimethylethyl ester To a solution of INTERMEDIATE 6 (1.5 g, 4.4 mmol) in dichloromethane (25 mL) was added thionyl bromide (0.36 mL, 4.6 mmol). After one hour at room temperature the reaction was washed with saturated aqueous sodium bicarbonate (100 mL) and the organic layer was separated. The aqueous layer was washed with dichloromethane (3×100 mL) and the combined organic extracts were dried ($Na_2SO_4$), filtered and concentrated.

The benzyl bromide was dissolved in acetonitrile (35 mL) and N-Boc piperazine (0.9 g, 4.8 mmol) and triethylamine (0.67 mL, 4.8 mmol) were added. After heating the reaction for one hour at 65° C. the reaction was cooled, washed with saturated amonium chloride/ethyl acetate and the organic layer was separated. The aqueous layer was extracted with ethyl acetate (3×100 mL) and the combined organic extracts were dried ($Na_2SO_4$), filtered and concentrated. The residue was purified by flash chromatography to give INTERMEDIATE 7 (2.04 g, 91%).

INTERMEDIATE 8: 3-[[4-[(diethylamino)carbonyl]phenyl][4(phenylmethyl)-1-piperazinyl]methyl]-benzoic acid, methyl ester To a solution of INTERMEDIATE 7 (2.0 g, 3.9 mmol) in dichloromethane (30 mL) was added trifluoroacetic acid (15 mL). After 10 minutes the reaction was concentrated and the residue dissolved in dichloromethane and washed with saturated aqueous sodium bicarbonate. The organic extract was dried ($MgSO_4$), filtered and concentrated.

The residue was dissolved in acetonitrile (25 mL) and benzyl bromide (475 μL, 4.0 mmol) and triethylamine (550 μL, 4.0 mmol) were added. After one hour at room temperature the reaction was concentrated, residue dissolved in dichloromethane and washed with water. The organic layer was dried ($MgSO_4$), filtered and concentrated to give INTERMEDIATE 8 (1.66 g, 85%).

INTERMEDIATE 9: 3-[[4-[(diethylamino)carbonyl]phenyl][4-(phenylmethyl)-1-piperazinyl]methyl]-benzoic acid To a solution of INTERMEDIATE 8 (1.66 g, 3.3 mmol) in methanol (15 mL) and water (5 mL) was added lithium hydroxide (0.69 g, 16.5 mmol). After 5 hours at room temperature the methanol was removed and INTERMEDIATE 9 was precipitated from the aqueous solution by the addition of 2M hydrochloric acid.

COMPOUND 1,1a AND 1b: 3-[(4-[(diethylamino)carbonyl]phenyl)(4-benzyl-piperazin-1-yl)methyl]benzamide

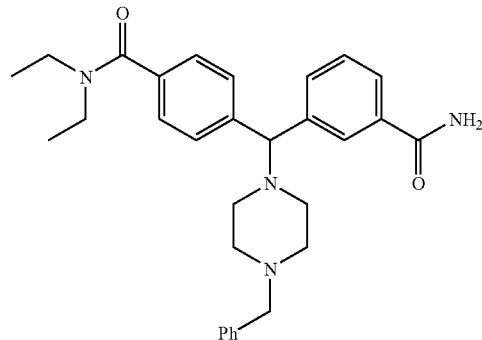

Compound 1: Racemic
Compound 1a: (−) Isomer
Compound 1b: (+) isomer

To a solution of INTERMEDIATE 4a (428 mg) in tert-butanol (10 mL) was added crushed potassium hydroxide (129 mg, 2.5 eq) and the reaction was heated to reflux. After 90 minutes the reaction was cooled and diluted with dichloromethane (40 mL). The reaction was washed with water (30 mL) and the organic layer separated. The aqueous layer was neutralized with 2 N hydrochloric acid and washed with dichloromethane (2×25 mL). The combined organic extracts were dried ($MgSO_4$), filtered and concentrated. The residue was purified by flash chromatography, eluting 3% methanol in dichloromethane to yield COMPOUND 1 as a colorless foam (374.5 mg, 84%). $^1$H NMR ($CD_3OD$) δ 1.06 (t, J=6.9 Hz, 3H), 1.20 (t, J=6.8 Hz, 3H), 3.15-3.40 (m, 6H), 3.545-3.54 (m, 2H), 3.57-3.67 (m, 4H), 4.44 (s, 2H), 5.39 (br s, 1H), 7.40 (d, J=8.4 Hz, 2H), 7.43-7.59 m, 6H), 7.82 (d, J=7.8 Hz, 3H), 7.93 (d, J=7.0 Hz, 1H), 8.22 (s, 1H).

COMPOUND 1 was separated by chiral HPLC to yield COMPOUNDS 1a and 1b, using a chiral AD column with 30% isopropanol 70% hexanes as an eluant, retention time being 11.3 minutes and 16.5 minutes for COMPOUNDS 1a and 1b, respectively.

For COMPOUND 1a, Purity (HPLC): >99%; Optical purity (Chiral HPLC): >99%; Found: C, 58.93; H, 6.65; N, 8.82. $C_{30}H_{36}N_4O_2 \times 3.2HCl \times 0.6H_2O$ has C, 58.87; H, 6.65; N, 9.15%.

For COMPOUND 1b, Purity (HPLC): >99%; Optical purity (Chiral HPLC): >99%; Found: C, 58.88; H, 6.68; N, 8.94. $C_{30}H_{36}N4O_2 \times 3.1HCl \times 0.8H_2O$ has C, 58.87; H, 6.70; N, 9.15%

COMPOUNDS 2, 2a and 2b: 3-{(4-[(diethylamino)carbonyl]phenyl)[4-(2-furylmethyl)-piperazin-1-yl]methyl}benzamide

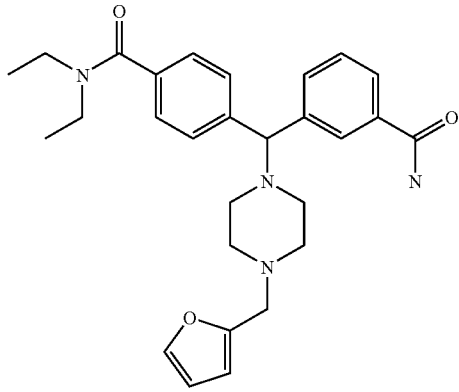

Compound 2: Racemic
Compound 2a: (-) isomer
Compound 2b: (+) isomer

To a solution of INTERMEDIATE 4b (365 mg) in tert-butanol (10 mL) was added crushed potassium hydroxide (112 mg, 2.5 eq) and the reaction was heated to reflux. After 90 minutes the reaction was cooled and diluted with dichloromethane (40 mL). The reaction was washed with water (30 mL) and the organic layer separated. The aqueous layer was neutralized with 2 N hydrochloric acid and washed with dichloromethane (2×25 mL). The combined organic extracts were dried (MgSO$_4$), filtered and concentrated. The residue was purified by flash chromatography to yield the racemic COMPOUND 2 as a colorless foam. $^1$H NMR (Free Amine) (400 MHz, CDCl$_3$): δ 1.09 (br s, 3H), 1.20 br s, 3H), 2.47 (m, 8H), 3.23 (br s, 2H), 3.52 (br s, 2H), 3.55 (s, 2H), 4.31 (s, 1H), 5.63 (br s, 1H), 6.10 (br s, 1H), 6.19 (d, J=2.9 Hz, 1 H), 6.30 (m, 1H), 7.27 (d, J=8.2 Hz, 2 H), 7.35 (m, 2H), 7.41 (d, J=8.2 Hz, 2 H) 7.59 (m, 2H), 7.84 (s, 1H).

COMPOUND 2 was separated by chiral HPLC to yield COMPOUNDS 2a and 2b, using a chiral AD column with 30% isopropanol 70% hexanes as an eluant, retention time being 9.9 minutes and 12.9 minutes for COMPOUNDS 2a and 2b, respectively.

For COMPOUND 2a, Purity (HPLC): >99%; Optical purity (Chiral HPLC): >99%. Found: C, 56.79; H, 6.65; N, 9.60. C$_{28}$H$_{34}$N$_4$O$_3$×2.6 HCl×1.3 H$_2$O has C, 56.73; H, 6.67; N, 9.45%.

For COMPOUND 2b, Purity (HPLC): >99%; Optical purity (Chiral HPLC): >99%. Found: C, 57.86; H, 6.54; N, 9.56. C$_{28}$H$_{34}$N$_4$O$_3$×0.7 HCl×3.1H$_2$O has C, 57.86; H, 6.76; N, 9.18%.

Alternative Synthesis of Compound 1

To a solution of INTERMEDIATE 9 (100 mg, 0.21 mmol) in dichloromethane (3 mL) at −20° C. was added isobutyl chloroformate (41 μL, 0.31 mmol) and triethylamine (43 μL, 0.31 mmol). After 10 minutes a solution of ammonia in dichloromethane (1.5M, 4.5 mL, 3 mmol) was added. Reacton was warmed to room temperature and washed with brine. The organic layer was dried (MgSO$_4$), filtered and concentrated to give COMPOUND 1.

COMPOUND 3, 3a AND 3b: 3-[[4-[(diethylamino)carbonyl]phenyl][4-(phenylmethyl)-1-piperazinyl]methyl]-N-methyl-benzamide

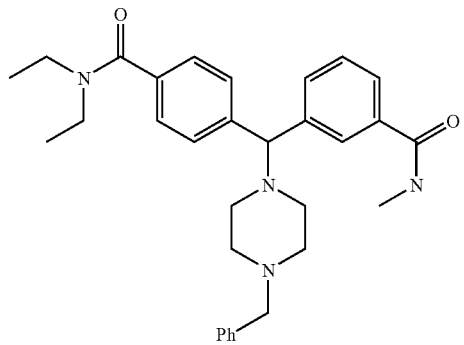

Compound 3: racemic
Compound 3a: (-) isomer
Compound 3b: (+) isomer

To a solution INTERMEDIATE 9 (0.120 mg, 0.25 mmol)) in 2 ml of DMF was added HATU (0.132 mg, 0.35 mmol) and diisopropylethylamine (173 μL, 0.99 mmol). The reaction was stirred for 30 minutes, after which was added (250 μL, 0.50 mmol) of 2 N HNCH$_3$ in MeOH and the stirring continued over night. The reaction was concentrated and partitioned between a saturated solution of NaHCO$_3$ and ethyl acetate. The organic layer was separated and the aqueous layer extracted 5 times with ethyl acetate. The organic layers were dried (MgSO$_4$), filtered and concentrated to yield COMPOUND 3. $^1$H NMR (400 NM, CD$_3$OD): δ 1.07 (m, 3H), 1.21 (m, 3H), 2.32 (m, 2H), 2.90 (s, 3H), 3.02 (m, 2H), 3.24 (m, 4H), 3.40 (m, 2H), 3.50 (m, 2H), 4.34 (s, 2H), 4.55 (s, 1H), 7.33 (d, J=8.2 Hz, 2 H), 7.41 (m, 1H), 7.48 (m, 5H), 7.56 (d, J=8.2 Hz, 2H), 7.63 (m, 2H), 7.93 (m, 1H)

COMPOUND 3 was separated by chiral HPLC to yield COMPOUNDS 3a and 3b, using a Chiralpak AD column with 35% isopropanol 65% Hexane as an eluent, retention time being 7.1 and 17.3 minutes for COMPOUNDS 3a and 3b respectively.

For COMPOUND 3a, Purity (HPLC):>99%; Optical purity (Chiral HPLC):>99%. Found: C, 59.20; H, 5.94; N, 8.26. C$_{31}$H$_{38}$N$_4$O$_2$×1.6 C$_2$HO$_2$F$_3$×0.7 H$_2$O has C, 59.21; H, 5.96; N, 8.08%

For COMPOUND 3b, Purity (BPLC):>97%; Optical purity (Chiral HPLC):>97%. Found: C, 59.73; H, 5.91; N, 8.32. C$_{31}$H$_{38}$N$_4$O$_2$×1.6C$_2$HO$_2$F$_3$×0.4 H2O: C, 59.68; H, 5.92; N, 8.14%

What is claimed is:

1. A compound of formula I, pharmaceutically acceptable salts thereof, or mixtures thereof:

I

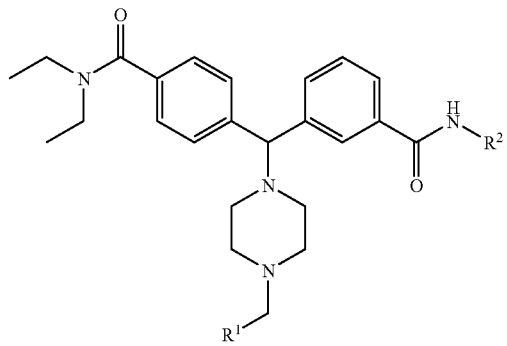

wherein

R$^1$ is C$_6$-C$_{14}$ aryl, five-membered ring heteroaryl, six-membered ring heteroaryl, or N-oxido-pyridyl, wherein said $C_6$-$C_{14}$ aryl five-membered ring heteroaryl, and six-membered ring heteroaryl are each independently and optionally substituted with one or more groups selected from $C_{1-6}$alkyl, halogenated $C_{1-6}$alkyl, —$NO_2$, —$CF_3$, $C_{1-6}$ alkoxy, chloro, fluoro, bromo, and iodo; and $R^2$ is hydrogen or $C_{1-12}$alkyl.

2. A compound according to claim 1, wherein $R^1$ is selected from phenyl; pyridyl; thienyl; furyl; imidazolyl; triazolyl; pyrrolyl; thiazolyl; and N-oxido-pyridyl, optionally substituted with one or more groups selected from $C_{1-6}$alkyl, halogenated $C_{1-6}$alkyl, —$NO_2$, —$CF_3$, $C_{1-6}$ alkoxy, chloro, fluoro, bromo, and iodo; and $R^2$ is hydrogen or methyl.

3. A compound according to claim 1, wherein $R^1$ is selected from phenyl; pyridyl; thienyl; furyl; imidazolyl; pyrrolyl; and thiazolyl, optionally substituted with one or more groups selected from $C_{1-6}$alkyl, halogenated $C_{1-6}$alkyl, —$NO_2$, —$CF_3$, $C_{1-6}$ alkoxy, chloro, fluoro, bromo, and iodo; and $R^2$ is hydrogen or methyl.

4. A compound according to claim 1, wherein $R^1$ is selected from phenyl; pyridyl; thienyl; furyl; imidazolyl; pyrrolyl; and thiazolyl; and $R^2$ is hydrogen or methyl.

5. A compound according to claim 1, wherein the compound is:

3-[(4-[(diethylamino)carbonyl]phenyl)(4-benzyl-piperazin-1-yl)methyl]benzamide;

3-{(4-[(diethylamino)carbonyl]phenyl)[4-(2-furylmethyl)-piperazin-1-yl]methyl}benzamide; or 3-[[4-[(diethylamino)carbonyl]phenyl][4-(phenylmethyl)-1-piperazinyl]methyl]-N-methyl-benzamide; or enantiomers thereof; or pharmaceutically acceptable salts thereof; or mixtures thereof.

6. A pharmaceutical composition comprising a compound according to claim 1 and a pharmaceutically acceptable carrier.

7. A method for the therapy of pain in a warm-blooded animal, comprising administering to said animal in need of such therapy a therapeutically effective amount of a compound according to claim 1.

8. A process for preparing a compound of formula II,

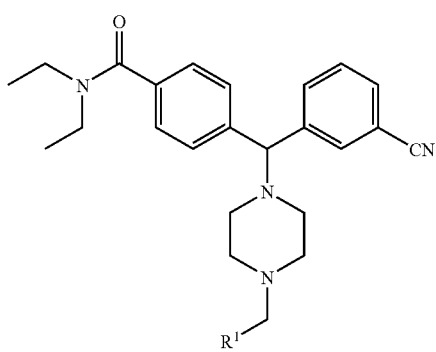

comprising reacting a compound of formula III:

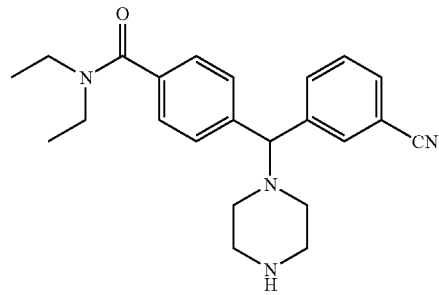

with $R^1$—CHO to form the compound of formula II
wherein
$R^1$ is $C_6$-$C_{14}$ aryl, five-membered ring heteroaryl, six-membered ring heteroaryl, or N-oxido-pyridyl, wherein said $C_6$-$C_{14}$ aryl five-membered ring heteroaryl, and six-membered ring heteroaryl are each independently and optionally substituted with one or more groups selected from $C_{1-6}$alkyl, halogenated $C_{1-6}$alkyl, —$NO_2$, $CF_3$, $C_{1-6}$ alkoxy, chloro, fluoro, bromo, and iodo.

9. A process for preparing a compound of formula IV,

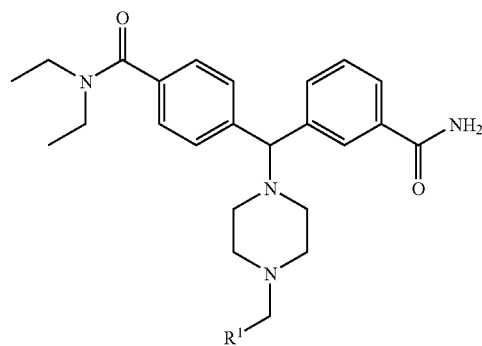

comprising: reacting a compound of formula II,

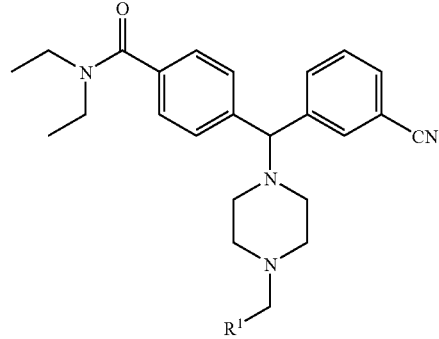

with an akali metal hydroxide in non-aqueous solvent to form the compound of formula IV:
wherein
$R^1$ is $C_6$-$C_{14}$ aryl, five-membered ring heteroaryl, six-membered ring heteroaryl, or N-oxido-pyridyl, wherein said $C_6$-$C_{14}$ aryl five-membered ring heteroaryl, and six-membered ring heteroaryl are each independently and optionally substituted with one or more groups selected from $C_{1-6}$alkyl, halogenated $C_{1-6}$alkyl, —$NO_2$, —$CF_3$, $C_{1-6}$ alkoxy, chloro, fluoro, bromo, and iodo.

* * * * *